United States Patent [19]

Karcher et al.

[11] Patent Number: 4,792,686
[45] Date of Patent: Dec. 20, 1988

[54] COLLIMATOR FOR TOMOGRAPHY

[75] Inventors: Gilles Karcher, Nancy; Max Amor, Vandoeuvre; Roger Niddam, Le Rancy; Jean-Pierre Villemot, Nancy, all of France

[73] Assignee: Medicorp Research Laboratories Corporation, Boca Raton, Fla.

[21] Appl. No.: 98,730

[22] Filed: Sep. 16, 1987

Related U.S. Application Data

[63] Continuation of Ser. No. 821,498, Jan. 22, 1986, abandoned.

[30] Foreign Application Priority Data

Jan. 28, 1985 [FR] France ................................ 85 01120

[51] Int. Cl.⁴ .......................... G01T 1/666; G21K 1/02
[52] U.S. Cl. .................................. 250/363 S; 378/151; 378/150
[58] Field of Search ........ 250/363 SH, 505.1, 363 SB, 250/363 SC; 378/149, 150, 151

[56] References Cited

U.S. PATENT DOCUMENTS

| | | | |
|---|---|---|---|
| 4,079,259 | 3/1978 | Blum | 378/149 |
| 4,181,839 | 1/1980 | Hatton et al. | 378/149 |
| 4,197,460 | 4/1980 | Anger | 378/149 |
| 4,419,763 | 12/1983 | Hawman | 378/149 |
| 4,597,096 | 6/1986 | Larsson | 378/149 |

Primary Examiner—Carolyn E. Fields
Attorney, Agent, or Firm—Darby & Darby

[57] ABSTRACT

A collimator for tomoscintigraphy comprising several juxtaposed sets of adjacent parallel tubes each positioned for each receiving transverse radiation at a different incidence angle from an individual organ under observation, thereby permitting with each step of rotation of a gamma camera, selective registration of information corresponding to as many images as there are sets in the collimator.

4 Claims, 2 Drawing Sheets

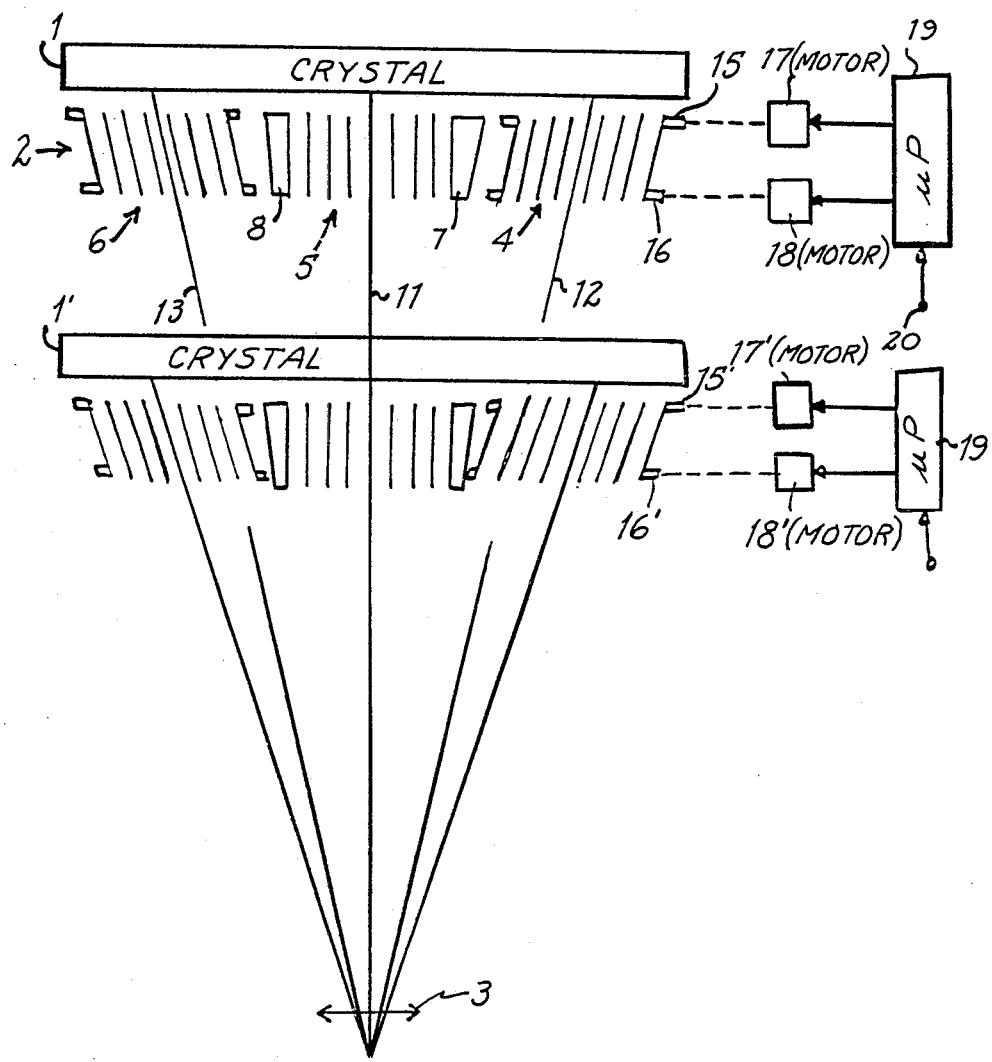

COLLIMATOR FOR TOMOGRAPHY

This is a continuation of application Ser. No. 821,498, filed Jan. 22, 1986, now abandoned.

FIELD OF THE INVENTION

The invention relates to a collimator for tomoscintigraphy. Tomoscintigraphy is a method of examination used in nuclear medicine in which scintigraphic images of an organ are recorded at a number of incidences, and cross sections of this organ are reconstructed by data processing.

BACKGROUND OF THE INVENTION

For the recording of scintigraphic images a scintillation camera or gamma camera is used. This gamma camera can rotate step by step on an axis passing through the organ to be examined, to record scintigraphic images at successive incidences, the number of which is generally 16, 32, 64 or 128. On the basis of the data collected during the rotation of the camera, an algorithm of tomographic reconstruction makes it possible to obtain a series of cross sections several millimeters thick.

With a conventional gamma camera, one scintigraphic image per incidence is recorded. As a result, the main drawback of tomoscintigraphy is the slowness of acquisition of the data.

SUMMARY OF THE INVENTION

The object of the invention is to reduce the total time of acquisition of the data by permitting the simultaneous production of several scintigraphic images at different incidences from a given position of the gamma camera, making it possible to reduce the number of steps in the rotation of the gamma camera.

The subject of the invention is a collimator for scintigraphy which is to be placed in front of the sensitive crystal of a scintillation or gamma camera, of the type having a plurality of adjoining, parallel tubes which are to be traversed lengthwise by the radiation from the organ observed, characterized in that it is constituted by several juxtaposed sets of tubes, each set having the direction of its tubes oriented toward the organ observed, this direction corresponding to that of the tube placed substantially in the center of the set, so as to define, for each set, an incidence corresponding to a scintigraphic image of the organ observed, in order that each step of rotation of the camera will be able to record data.

According to other characteristics of the invention:

each lateral set of tubes comprises a plurality of parallel tubes whose ends are held by two grid that can move parallel to one another in an articulated frame, each of the grids is commanded by an electric motor which in turn is under the control of a microprocessor, the microprocessor commands the electric motors as a function of the data kit receives on the distance from the camera to the organ observed.

BRIEF DESCRIPTION OF THE DRAWINGS

By way of example, and to facilitate understanding of the description, the attached drawing shows, in which like items have the same reference designation:

FIG. 2, a view in cross section of the collimator in FIG. 1, in two positions corresponding to two measuring distances.

DESCRIPTION OF THE PREFERRED EMBODIMENT

Figure 1:
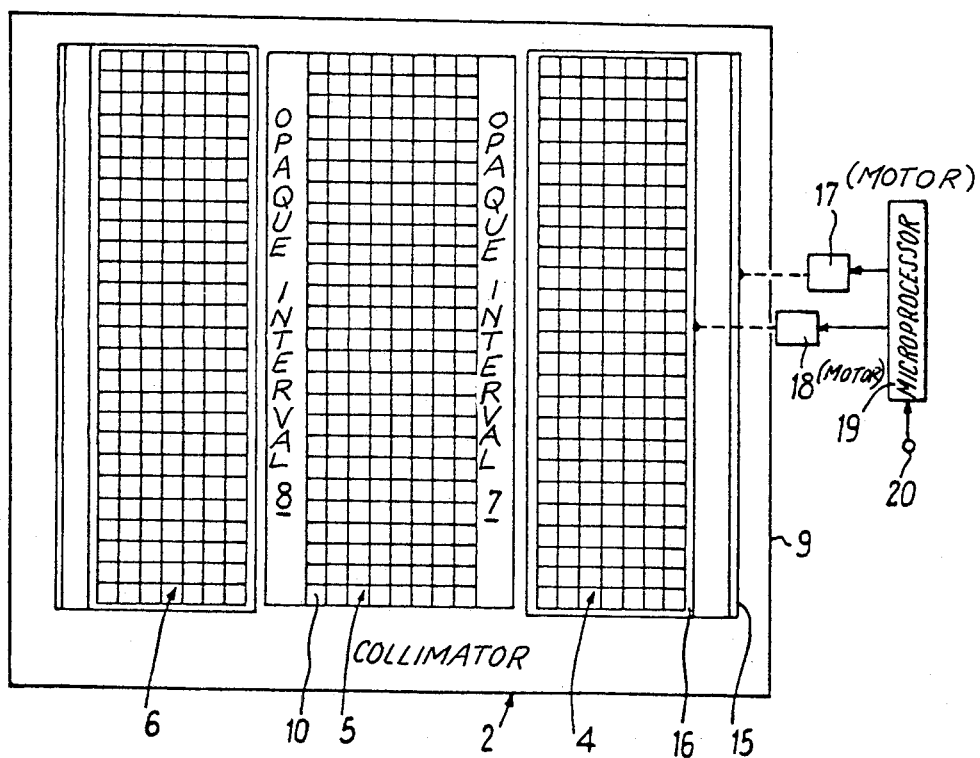
FIG. 1, a front view of an example of embodiment of a collimator according to the invention.

The collimator according to the invention is meant to be placed in front of the detector crystal of the gamma camera. This crystal is generally a monocrystal, for example of sodium iodide doped with thallium, which scintillates when it receives the radiation from the organ observed. In order to be limited precisely to this direct radiation, while eliminating diffuse radiations, a collimator is placed in front of this crystal, said collimator being constituted by a plurality of adjoining, parallel tubes, with a square section, for example, and separated by partitions which are preferably made of lead.

According to the invention, the sensitive crystal of the gamma camera is represented at 1 (FIG. 2) and the collimator at 2. The organ under observation is symbolized at 3. The collimator 2 (FIG. 1) is constituted by three sets 4, 5, 6 separated by opaque intervals 7, 8. Each set 4, 5, 6, is constituted by a plurality of parallel tubes. These tubes such as 10 (FIG. 1) are square in cross section in the example represented. Their walls are made of lead, for example. The length of the tubes is on the order of 3 to 10 cm, their width on the order of 2 to 6 mm and the thickness of their separation wall on the order of 0.2 to 2 mm in the example of embodiment described.

For each set the tubes are all parallel. Set 5 which is placed in the central zone of the crystal 1 is constituted by tubes whose direction is perpendicular to the plane of the crystal so as to coincide with the direction of radiation 11 from the organ under observation.

The tubes in set 4 are inclined to crystal 1 so that their direction coincides with that of radiation 12. Likewise, the direction of the tubes in set 6 coincides with that of radiation 13. Radiations 12 and 13 form a well defined angle with the direction of radiation 11. This angle, which corresponds to a well defined incidence is selected as the angle of inclination of the tubes in the corresponding unit on the perpendicular to the sensitive crystal.

Each set of tubes 4, 5, 6 is disposed in the collimator so that the corresponding radiation, respectively 12, 11, 13, will terminate in the tube placed substantially in the center of the set. In so doing, each set of tubes makes it possible to form a scintigraphic image corresponding to a given incidence.

In the example represented, the collimator comprises three sets and for each step of rotation of the gamma camera the latter will collect three scintigraphic images of the organ under observation.

Thus, when adapted to an existing rotary gamma camera, hence without a heavy investment, the collimator according to the invention makes it possible to substantially reduce the number of steps of rotation for the acquisition of the same number of scintigraphic images. The result is a shorter dwell of the gamma camera for each observation.

The angle selected for the directions of radiation 12 and 13 relative to the direction of radiation 11 depends on the total number of incidences desired for the observation. The length of the tubes, their diameter and the thickness of their separating partition are selected as a function of the conditions of experimentation. The parameters to be taken into consideration for this experimentation are, in particular: the energy of radiation emitted by the organ under observation, the volume of this organ and the resolution desired for the image.

With a gamma camera of conventional type, scintigraphic images can be registered at successive incidences by proceeding by rotation step by step around the organ to be observed. This rotation can be accompanied by a variation in the distance from the camera to the organ to be observed. In this case as a general rule, the camera moves not in a circle but in an ellipse, for example.

FIG. 2 shows two positions of the camera corresponding to two different distances relative to the organ observed, again symbolized at 3. In the distant position, the crystal bears the reference 1, and in the near position, the reference 1'. To insure the correct orientation of the tube sets 4 and 6 as a function of the distance to the object to be observed, these sets are mounted on articulated frames which can be varied as to inclination, so that the tubes in one set 4, 6 are always parallel to the direction of radiation 12, 13, respectively, passing through the center of the corresponding tube set. In this way the intersection of the directions of the tube sets is always at the center of rotation of the camera.

To retain the same image quality in the course of the elliptical rotation of the camera, it is preferable that the scintigraphic images always be formed in the same place on the crystal. It is therefore not enough to pivot the tubes around axes passing through their center. According to the invention, the sets of tubes are mounted between two grids 15, 16 placed in the vicinity of their ends, one, 6, toward the organ to be observed, the other, 5, toward the crystal 1. These two grids are disposed in an articulated frame and are designed to be moved relative to one another while remaining parallel to one another and to the crystal 1. Each one is commanded by an electric motor 17, 18 respectively, that moves them as a function of the distance between the organ to be observed and the gamma camera. The two motors 17, 18 have a fixed position relative to the frame 9 of the collimator assembly. Thus grids 15, 16 are displaced relative to this frame so that the point of impact on crystal 1, of the middle rays 12, 13, will always be in the same place. By way of example, the position of the gamma camera closest to or furthest from, the organ, can be fixed in advance and the corresponding position of the grids and the sets of tubes likewise. The radial displacements of the camera can be measured by a sensor that transmits the corresponding data 20 to a microprocessor 19, for example. Software permits commanding the electric motors 17, 18, to place the tubes in the desired inclination. If the camera is also commanded in its displacements by software, this same software can command the motors 17, 18.

With the gamma camera according to the invention it is therefore possible to reduce the number of stages in the process of acquisition of data, and even when the distance from the camera to the organ under observation varies, it is possible to produce several scintigraphic images simultaneously at different incidences from a given position of the gamma camera.

We claim:

1. Collimator for tomoscintigraphy, which is to be placed in front of the sensitive crystal of a gamma camera, of the type comprising a plurality of adjacent parallel tubes to be traversed lengthwise by the radiation from the organ under observation, characterized in that it is constituted by several juxtaposed sets of tubes, each set of tubes having the direction of its tubes selectively oriented toward the same organ under observation via orientation means for controlling the orientation, this direction corresponding to that of the tube placed substantially in the center of the set, so as to define, for each set, an incidence angle corresponding to a scintigraphic image of the organ under observation, so as to permit with each step of rotation of the gamma camera, selective registration of information corresponding to as many images as there are sets in the collimator.

2. Collimator according to claim 1, characterized in that each lateral set of tubes comprises a plurality of parallel tubes whose ends are held by two grids including said orientation means for selectively moving the two grids parallel to one another within an articulated frame.

3. Collimator according to claim 2, wherein said orientation means further includes drive means for moving said grids, said drive means including an electric motor, and a microprocessor for controlling said motor in moving said grids.

4. Collimator according to claim 3, characterized in that the microprocessor includes programming means for controlling said electric motors as a function of the distance from the camera to the organ under observation.

* * * * *